United States Patent [19]

Ruderian

[11] Patent Number: 4,722,326
[45] Date of Patent: Feb. 2, 1988

[54] VIBRATORY THERAPEUTIC DEVICE

[76] Inventor: Max J. Ruderian, 545 Hanley Ave., Los Angeles, Calif. 90049

[21] Appl. No.: 817,697

[22] Filed: Jan. 13, 1986

Related U.S. Application Data

[63] Continuation-in-part of Ser. No. 794,525, Nov. 4, 1985, abandoned, which is a continuation-in-part of Ser. No. 701,745, Feb. 14, 1985, Pat. No. 4,596,565, and a continuation-in-part of Ser. No. 702,800, Feb. 19, 1985, abandoned, and a continuation-in-part of Ser. No. 719,063, Apr. 2, 1985, Pat. No. 4,587,959, and a continuation-in-part of Ser. No. 757,380, Jul. 22, 1985, Pat. No. 4,640,284, and a continuation-in-part of Ser. No. 757,381, Jul. 22, 1985, Pat. No. 4,597,757, and a continuation-in-part of Ser. No. 811,279, Dec. 20, 1985, Pat. No. 4,653,494.

[51] Int. Cl.⁴ ............................................. A61H 15/02
[52] U.S. Cl. ..................................... 128/24.1; 128/36; 128/57; 401/2; 401/209
[58] Field of Search ...................... 401/1, 2, 209, 215; 128/24.1–24.4, 56, 57, 36

[56] References Cited

U.S. PATENT DOCUMENTS

| | | |
|---|---|---|
| Re. 29,613 | 4/1978 | Kropfhammer . |
| 736,111 | 8/1903 | Kautz . |
| 900,602 | 9/1907 | Shelton . |
| 1,262,669 | 1/1917 | Hirota . |
| 1,697,080 | 1/1929 | Oppenheimer . |
| 1,772,501 | 8/1930 | Shelton . |
| 1,819,123 | 8/1931 | Robinson . |
| 1,825,118 | 9/1931 | Jaeg . |
| 1,856,811 | 5/1932 | Inaki . |
| 1,886,247 | 2/1934 | Borden . |
| 1,899,770 | 2/1933 | Oppenheimer . |
| 1,911,468 | 5/1933 | Robinson . |
| 1,947,042 | 2/1934 | Glennan ............................ 128/24.3 |
| 1,965,918 | 4/1932 | Auberger . |
| 1,969,042 | 8/1934 | Senn . |
| 2,018,046 | 10/1935 | Wilson . |
| 2,048,712 | 7/1936 | Schramm . |
| 2,067,979 | 1/1937 | Newton . |
| 2,081,034 | 1/1935 | Carter . |
| 2,136,844 | 11/1938 | Fair et al. . |
| 2,221,972 | 11/1940 | Jones et al. . |
| 2,226,582 | 12/1940 | Robinson . |
| 2,249,500 | 2/1940 | Shirley et al. . |
| 2,267,547 | 12/1941 | Zimmerman . |
| 2,280,992 | 4/1942 | Wright et al. . |
| 2,285,105 | 6/1942 | Laszlo ................................ 128/24.3 |
| 2,426,281 | 8/1945 | Oakes . |
| 2,451,540 | 9/1945 | Dinyer . |
| 2,470,297 | 5/1949 | Fields . |
| 2,574,945 | 11/1951 | Werner . |

(List continued on next page.)

FOREIGN PATENT DOCUMENTS

| | | |
|---|---|---|
| 517776 | 12/1929 | Fed. Rep. of Germany . |
| 718287 | 12/1950 | Fed. Rep. of Germany . |
| 2502821 | 1/1975 | Fed. Rep. of Germany . |
| 2749883 | 5/1979 | Fed. Rep. of Germany ..... 128/24.1 |
| 3139848 | 4/1983 | Fed. Rep. of Germany . |
| 704302 | 2/1931 | France . |
| 288838 | 4/1930 | Italy . |
| 135345 | 11/1929 | Switzerland ....................... 128/24.3 |
| 13825 | of 1905 | United Kingdom . |
| 526678 | 9/1940 | United Kingdom . |
| 2082124 | 3/1982 | United Kingdom ................ 401/209 |

*Primary Examiner*—Clyde I. Coughenour
*Attorney, Agent, or Firm*—Kelly, Bauersfeld & Lowry

[57] ABSTRACT

An improved vibratory therapy device is provided for use in relieving muscular and/or joint discomfort, stress, and the like. The vibratory therapy device comprises a lightweight portable housing encasing a heater/vibrator assembly for imparting vibratory action to a massage head together with heated air flow. A plurality of interchangeable massage heads are disclosed, including, for example, smooth or roughened surface textures, single or multiple roller balls, and the like. Other massage head forms may include a medicant applicator or a nasal inhaler unit. A flexible carrying bag is also provided and optimally can be mounted onto the housing to define a depending skirt for concentrating heat flow against a selected region of a person's body receiving massage therapy.

8 Claims, 13 Drawing Figures

U.S. PATENT DOCUMENTS

| | | | |
|---|---|---|---|
| 2,598,525 | 5/1952 | Fox . | |
| 2,674,994 | 4/1954 | Murphy | 128/36 |
| 2,706,988 | 4/1955 | Weber . | |
| 2,739,586 | 3/1956 | Preis . | |
| 2,787,998 | 4/1957 | Grossi et al. . | |
| 3,096,757 | 7/1963 | Berard . | |
| 3,163,166 | 12/1964 | Brant | 401/209 |
| 3,308,268 | 4/1965 | Laing . | |
| 3,370,583 | 2/1965 | Teranishi . | |
| 3,481,326 | 4/1967 | Schamblin . | |
| 3,648,368 | 3/1972 | Douglass et al. . | |
| 3,710,785 | 1/1973 | Hilger . | |
| 3,752,155 | 8/1973 | Blinoff, Jr. et al. . | |
| 3,861,364 | 1/1975 | Greenfield . | |
| 4,025,809 | 5/1977 | Teranishi . | |
| 4,111,567 | 9/1978 | Berghahn | 401/215 |
| 4,173,231 | 11/1979 | Isino et al. . | |
| 4,248,218 | 2/1981 | Fischer . | |
| 4,365,426 | 12/1982 | Suzuki et al. . | |
| 4,367,735 | 1/1983 | Dali . | |
| 4,399,349 | 8/1983 | Deming et al. . | |
| 4,403,611 | 9/1983 | Babbitt et al. . | |
| 4,430,808 | 2/1984 | Toyomi et al. . | |
| 4,468,221 | 8/1984 | Mayfield . | |
| 4,523,589 | 6/1985 | Krauser . | |

U.S. Patent    Feb. 2, 1988    Sheet 1 of 3    4,722,326
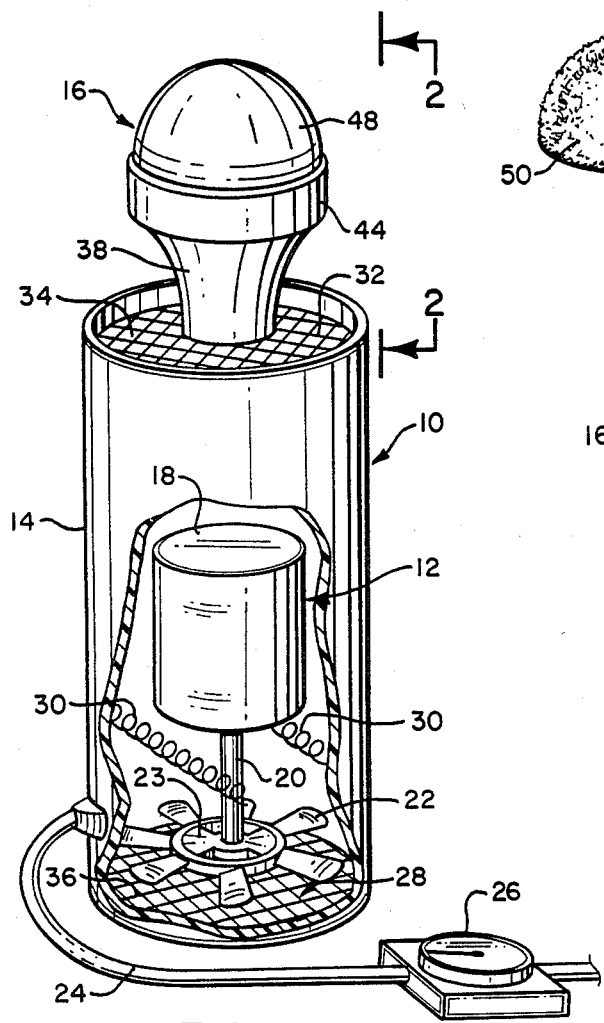
FIG.1
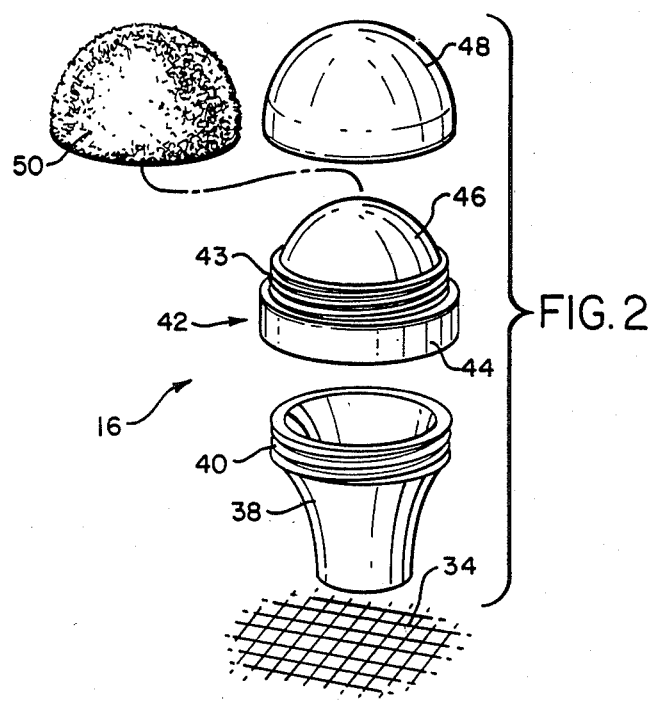
FIG.2
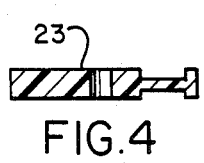
FIG.4
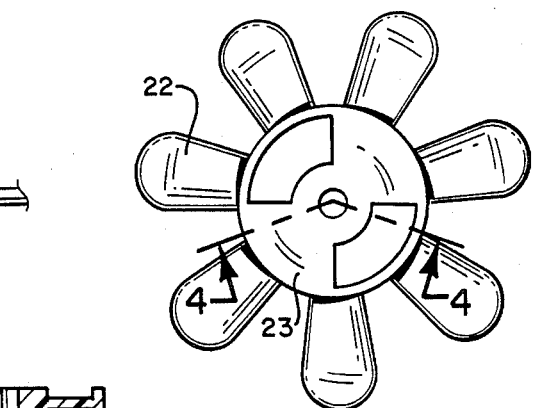
FIG.3
FIG.5    FIG.6    FIG.7

VIBRATORY THERAPEUTIC DEVICE

BACKGROUND OF THE INVENTION

This application is a continuation-in-part of copending application Ser. No. 794,525, filed Nov. 4, 1985, now abandoned which is in turn a continuation-in-part of copending application Ser. Nos. 701,745, filed Feb. 14, 1985, now U.S. Pat. No. 4,596,565; 702,800, filed Feb. 19, 1985, now abandoned; 719,063, filed Apr. 2, 1985 now U.S. Pat. No. 4,587,959; 757,380, filed July 22, 1985, now U.S. Pat. No. 4,640,284; and 757,381, filed July 22, 1985, now U.S. Pat. No. 4,597,757. In addition, this application is a continuation-in-part of copending application Ser. No. 811,279, filed Dec. 20, 1985, now U.S. Pat. No. 4,653,494.

This invention relates generally to therapeutic devices designed primarily for massage therapy to relieve muscular and/or joint discomfort and the like. More particularly, this invention relates to improved designs for relatively lightweight, portable, and inexpensive vibratory therapy devices.

Vibratory devices in general are known for use in applying vibratory therapy to selected regions of the body. Such devices have typically included a motor-driven vibrator unit for imparting a physically detectable vibratory motion to an externally exposed head which, when placed against the body, can be effective to ease muscular discomfort, stress, and the like. As disclosed and claimed in the above-referenced Ser. Nos. 794,525 and 757,381, such vibratory devices can be combined with a source of heated air flow for providing an enhanced and highly soothing therapeutic effect.

The present invention relates to further improvements in therapeutic vibratory devices to enhance the utility and soothing effects thereof. Moreover, the present invention relates to simplified vibratory device constructions adapted for use in a broad variety of therapeutic applications and adapted to include a plurality of easily interchanged massage heads.

SUMMARY OF THE INVENTION

In accordance with the invention, an improved vibratory therapeutic device is provided in the form of a relatively lightweight and highly portable housing encasing a compact heater/vibrator assembly. The heater/vibrator assembly imparts, in operation, a therapeutic vibratory action to the entire device including a removably mounted massage head of selected design. In addition, heated air flow is provided in and around the message head to cooperate with the vibratory action when the massage head is placed against the body for a soothing therapeutic effect.

In one preferred form of the invention, the heater/vibrator assembly comprises a lightweight electric motor or the like encased within the housing for rotatably driving an output shaft carrying an eccentrically weighted fan. Rotational driving of the fan upon appropriate connection of the motor to a suitable electrical power supply results in vibratory motion of the entire device and further produces a flow of air through the housing from an air intake to an air outlet. Heating elements within the housing are provided to heat this air flow for discharge flow through the air outlet to the region in and about the massage head. Control means, such as a rheostat may be provided to regulate air flow rate and discharge temperature.

In one form, the massage head comprises a mounting base secured on the housing generally at the air outlet. This mounting base removably supports a roller ball assembly carrying one or more roller balls for rolling movement over a portion of a person's body being treated. Vents and/or air passages formed in the mounting base and ball assembly may be provided for enhanced air flow action in and about the message head. Alternately, the mounting base can be adapted to contain a supply of a selected medicant for application to the person's body via the roller ball assembly.

One or more massage caps of different surface characteristics such as smooth or rough textured hemispherical caps can be provided for removable mounting onto the mounting base on the roller ball assembly. When so mounted, the selected massage cap provides a non-rolling or statioary massage head configuration which can be moved over the portion of a person's body being treated. When multiple massage caps are provided, a non-selected massage cap can be removably mounted in a storage position at another location on the lightweight housing.

In still another form of the invention, a nasal inhalator unit can be provided for removable mounting onto a hollow massage head mounting base. The nasal inhalator unit includes means for removably supporting a medicant-containing inhalation tube. During opertion, warm air flow from the housing air outlet passes through the nasal inhalator unit, including the nasal inhalation tube to vaporize the medicant and carry same outwardly for direction into a person's nasal passages.

A flexible carrying bag is advantageously included for use in transporting and storing the vibratory device. In a preferred form, the bag includes an upper end adapted to fasten about a midportion of the housing and a lower end which can be opened to permit air flow therethrough. When installed on the housing in this manner, the bag forms a depending skirt draped about the housing to concentrate air flow against a selected portion of the body being treated.

Other features and advantages of the present invention will become more apparent from the following detailed description, taken in conjunction with the accompanying drawing, which illustrate, by way of example, the principles of the invention.

BRIEF DESCRIPTION OF THE DRAWINGS

The accompanying drawings illustrate the invention. In such drawings:

FIG. 1 is a fragmented perspective view illustrating a vibratory therapy device embodying the novel features of the invention;

FIG. 2 is an exploded perspective view illustrating construction details of a preferred massage head for the vibratory therapy device of FIG. 1;

FIG. 3 is an enlarged plan view illustrating a preferred fan for use in the vibratory device;

FIG. 4 is a vertical sectional view taken generally on the line 4—4 of FIG. 3;

FIG. 5 is an enlarged exploded perspective view illustrating an alternative massage head for use in the vibratory device of FIG. 1;

FIG. 6 is a top plan view of the massage head of FIG. 5;

FIG. 7 is a fragmented perspective view illustrating an alternative housing configuration for the vibratory device;

DETAILED DESCRIPTION OF THE PREFERRED EMBODIMENTS

Figure 8:
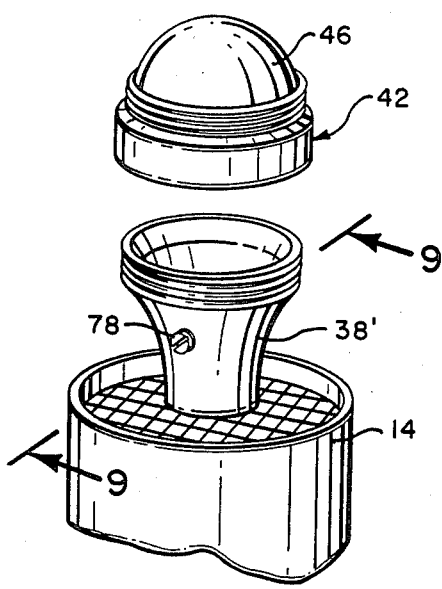
FIG. 8 is a fragmented exploded perspective view similar to FIG. 1 and illustrating a further alternative form of a massage head.

As shown in the exemplary drawings, a vibratory therapy device embodying one preferred form of the invention is designated generally by the reference numeral 10 in FIG. 1. The vibratory device 10 includes a combination heater/vibrator assembly 12 mounted within a lightweight, portable housing 14 to impart vibratory motion in conjunction with heated air flow to a massage head 16 of selected configuration. The particular geometry of the message head is adapted for rapid interchanging to alter the specific therapeutic effects as desired or required by the person receiving massage therapy.

As shown best in FIG. 1, the improved vibratory therapy device 10 comprises the lightweight housing 14 of illustrative generally cylindrical shape and which is advantageously formed from a lightweight and relatively inexpensive impact-resistant molded plastic or the like. The heater/vibrator assembly 12 is mounted within the housing in any suitable manner and includes a lightweight motor 18 for rotatably driving an output shaft 20. An air flow fan 22 of lightweight molded plastic or the like is securely mounted upon the output shaft 20 for rotation therewith upon appropriate connection of the motor 18 to a source of electrical power. A power cord 24 is shown in FIG. 1 for this purpose and may be appropriately connected to an ac or cc power supply, as required, with an adjustable theostat 26 being mounted along the power cord 24 to provide a combination on-off switch and to regulate the rotational speed of the motor 18 and fan 22.

Rotational driving of the air flow fan 22 functions to draw air into the housing 14 through a rearwardly upon air intake 28. This air flows through the housing 14 past appropriately mounted heating elements 30 which are also coupled to the power supply through the rheostat 26, whereby the rheostat also regulates heating of the air flow. From the heating elements 30, the air flows further through the housing for discharge therefrom through an air outlet 32 shown in FIG. 1 to include a perforated safety screen 34 upon which the massage head 16 is securely mounted. Accordingly, the heated air flow discharged through the air outlet 32 flows in and around the massage head 16. An additional safety screen 36 of similar design is normally provided over the air intake 28.

In accordance with one primary aspect of the invention, rotation of the fan 22 also functions to impart vibratory action to the entire device including the massage head 16. More particularly, as shown best in FIGS. 3 and 4, the fan 22 includes a plurality of fan blades carried by a central hub 23 which is unbalanced or eccentrically weighted, for example, by forming the hub 23 with significantly different material thickness on opposite sides of a rotational axis. Accordingly, when the fan 22 is rotated, the unbalanced hub 23 causes a significant vibration of the entire device, wherein this vibration is controlled in frequency and magnitude by appropriate adjustment of the rheostat 26.

According to a further primary feature of the invention, the massage head 16 is rapidly adaptable to provide different massage surface configurations for contact with the skin of a person receiving massage therapy. For example, the preferred massage head construction accommodates both rolling and non-rolling massage surface configurations which can be interchanged rapidly without the use of any special tools. Accordingly, the specific nature of the massage surface can be uniquely tailored as desired or required by the person receiving massage therapy.

More specifically, as shown best in FIG. 2, the examplary massage head 16 comprises a massage head base 38 of generally cylindrical configuration with a lower end securely mounted by an adhesive or other suitable fastening means onto the air outlet safety screen 34 in a generally centered position. In the preferred form, this base 38 is hollow and extends upwardly from the safety screen 34 with a gradually increasing cross-sectional size. The upper end of the base 38 terminates with an external thread configuration 40 adapted for interchangeable mounting of different massage head elements.

A roller ball assembly 42 is normally mounted onto the upper end of the massage head base 38 and provides at least one rolling massage surface for smooth, non-wrinkling massaging action with the skin of a person receiving therapy. In particular, as viewed in FIG. 1, the roller ball assembly 42 comprises a downwardly open and internally threaded ball case 44 for threaded attachment onto the base 38. A relatively large roller ball 46 is rollingly supported within the ball case 44 and defines the rolling massage surface.

The roller ball assembly 42 is adapted in turn for removable mounting of a massage cap which may be provided in alternative forms with different surface textures. That is, as shown in FIG. 2, one massage cap 48 of generally hemispherical construction has a downwardly open and internally threaded geometry for rapid mounting onto the roller ball assembly 42 by means of external threads 43 on the ball case 44. Alternately, the massage cap 48 can be threaded directly onto the upper end of the massage head base 38. In either case, the massage cap 48 has an upwardly presented and generally hemispherical smooth surface configuration defining a smooth non-rolling massage surface for the vibratory device. If desired, however, the massage cap 48 can be interchanged with a similar alternative massage cap 50 differing only in the provision of a rough-surfaced external texture to provide still another massage surface configuration.

As shown in FIGS. 5 and 6, an alternate roller ball assembly 52 may also be provided in addition to or in substitution for the roller ball assembly 42 depicted in FIG. 2. More specifically, the alternate roller ball assembly 52 includes a modified ball case 54 which is downwardly open and internally threaded for rapid attachment to the massage head base 38. The upper end of the modified ball case 54 is defined by a transverse platform 56 supporting a plurality of upstanding ball supports 58 secured thereto and each carrying a relatively small roller ball 60, three of which are depicted in the exemplary drawings. These roller balls 60 thus provide still another configuration for a massage surface which is uniquely adapted to provide contoured rolling action around small or hard-to-reach surface areas of the body, for example, in and around fingers and toes. The therapeutic action of these roller balls 60 is greatly enhanced by providing multiple air flow vents 62 in the platform 56 to accommodate air flow passage upwardly through the base 38 in and around the small roller balls 60. In addition, external threads 64 on the modified ball case 54 are desirably provided to accommodate rapid mounting of a selected massage cap, such as a massage cap 48 or 50 depicted in FIG. 2.

If desired, the lightweight housing 14 of the vibratory device 10 can be modified, as viewed in FIG. 7, to provide storage capability for additional massage caps or roller ball assemblies when the device is not in use. For example, a modified cylindrical housing 14′ can be provided to include external threads 66 formed about the air intake 28. The size and shape of these threads can be selected to removably retain one of the massage caps or roller ball assemblies depicted in FIGS. 2, 5, and 6, with other massage caps and/or roller ball assemblies normally secured onto the massage head mounting base 38. The device thus supports for storage multiple massage head configurations, with the stored components being removed from the lower end of the housing 14′ during use to prevent interference with housing air flow.

Figure 9:
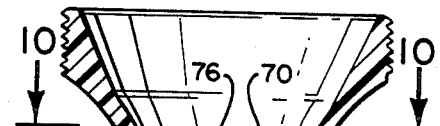
FIG. 9 is an enlarged fragmented vertical sectional view taken generally on the line 9—9 of FIG. 8.
Figure 9:
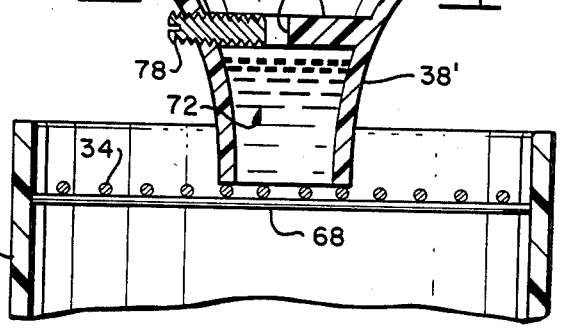
Figure 10:
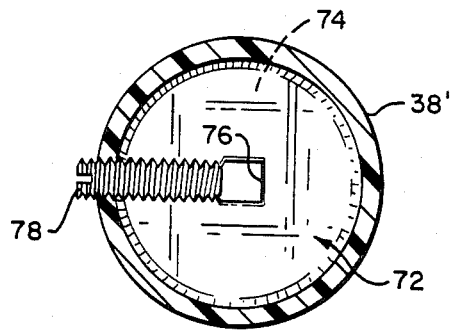
FIG. 10 is a horizontal sectional view taken generally on the line 10—10 of FIG. 9.

A further modified form of the invention is shown in FIGS. 8-10 to include a modified mounting base 38′ for removably supporting a roller ball assembly 42 or the like. In this form, the modified mounting base 38′ includes a lower wall 68 (FIG. 9) cooperating with an intermediate barrier wall 70 to define a well or chamber 72 within which a supply of a selected medicant 74 can be stored. The barrier wall 70 is interrupted by a vertically open gap 76 which is approximately threaded to receive a set screw 78 or the like having a protruding head accessible from the exterior of the mounting base 38′. Advancement or retraction of the set screw 78 thus variably opens or closes the gap 76 to regulate medicant flow to the roller ball 46 of the ball assembly 42 during massage action, thereby applying the medicant to the skin of a person receiving massage therapy. Alternately, the set screw 78 can be retracted sufficiently to permit relatively easy refilling of the well 72 with the selected medicant.

Figure 11:
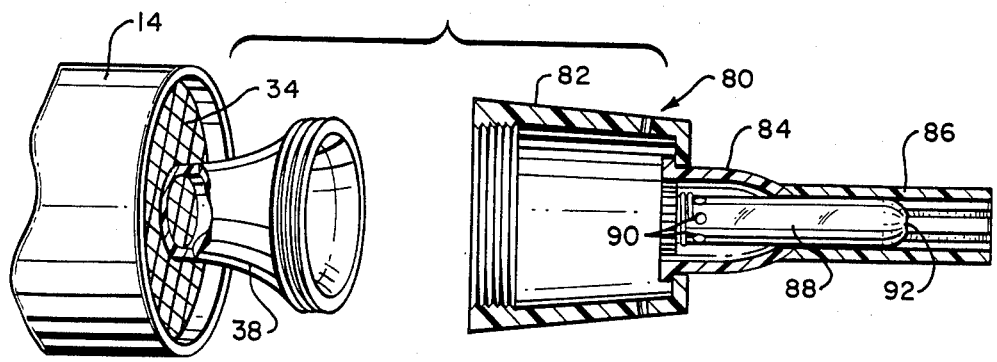
FIG. 11 is a fragmented exploded perspective view illustrating a further alternative form of the invention including a nasal inhalator unit.

In a still further form of the invention, the hollow mounting base 38 as described with respect to FIGS. 1 and 2 can be adapted for receiving a nasal inhalator unit 80 in lieu of the above-described massage surface components. As shown in FIG. 11, this nasal inhalator unit comprises an internally threaded cap 82 for receiving a supply of heated air through the mounting base 38. This heated air flows further into a forward support nozzle 84 at a forward end of the cap 82. As described in applicant's copending application Ser. No. 811,279, now U.S. Pat. No. 4,653,494, this support nozzle 84 has a relatively large cross section upstream end and tapers progressively to a small cross section downstream end which in turn is joined to a forwardly extending vented support sleeve 86. A standard medicant-containing inhalation tube 88 is adapted for rapid press-fit reception into the support nozzle 84 and support sleeve 86, whereby the heated air flow is directed into the inhalation tube via intake passages 90 and for discharge from the inhalation tube through an exit port 92. During passage through the inhalation tube, the heated air flow vaporizes and picks up a portion of the medicant which can then be discharged directly into a person's nasal passage, all in the manner described in applicant's copending application Ser. No. 811,279, now U.S. Pat. No. 4,653,494 which is incorporated by reference herein. Accordingly, the nasal inhalator unit 80 permits adaptation of the vibratory therapy device 10 for additional use in providing nasal inhalation therapy.

Figure 12:
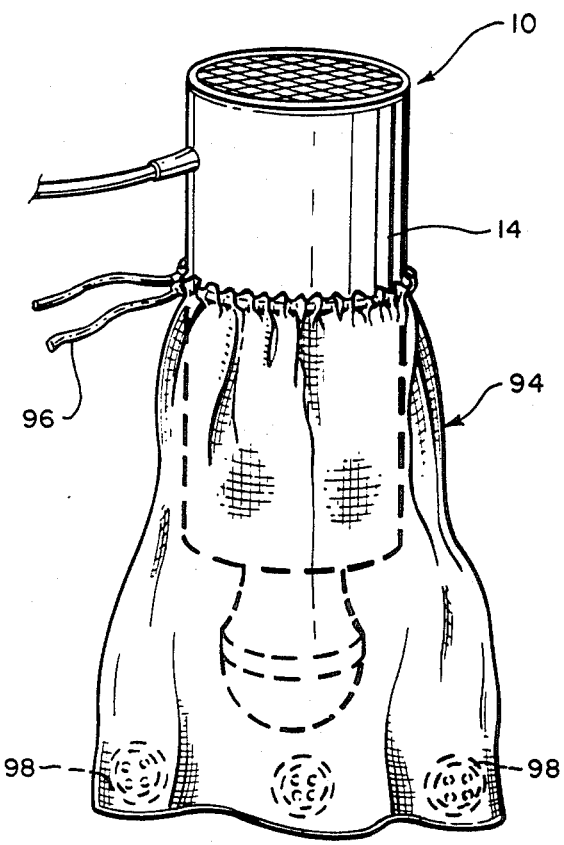
FIG. 12 is a perspective view illustrating a flexible carrying bag utilized as a heat flow concentrating hood or skirt.
Figure 13:
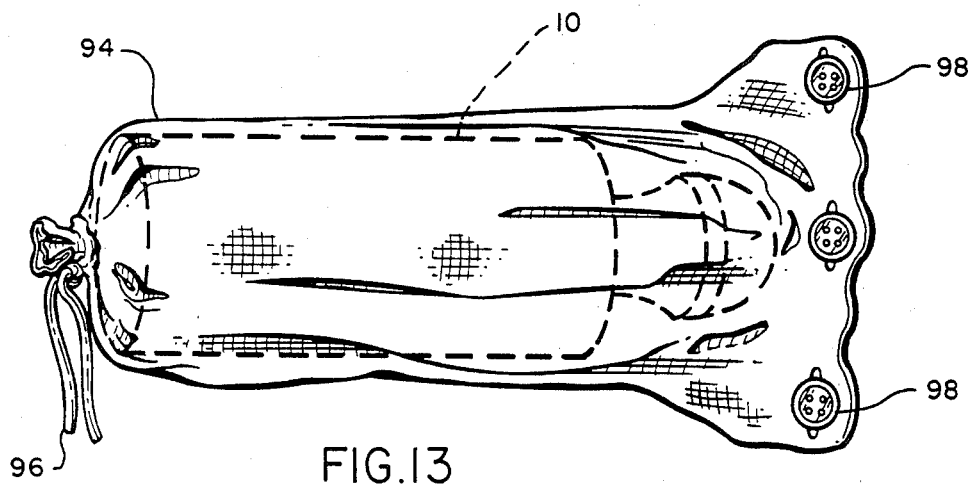
FIG. 13 is a perspective view illustrating the carrying bag with the vibratory device received therein.

As shown in FIGS. 12 and 13, the vibratory device 10 is conveniently provided with a flexible carrying bag 94 adapted for the dual functions of transporting the device and providing a heat concentration hood or skirt. More specifically, as viewed in FIG. 12, the upper end of the bag 94 is open and includes a drawstring 96 or the like for secure mounting about a midportion of the housing 14. In this position, the bag drapes as a skirt below the massage head and has an open lower end. Heated air flow from the device is thus concentrated in and about the region of the body being treated. However, when treatment is concluded, the bag 94 can be disassembled from the device and the bag lower end closed by means of buttons 98 or the like. The device 10 and any accessories can then be placed into the bag 94 for transport and/or storage, with the drawstring 96 effectively closing the bag upper end.

The improved vibratory therapy device 10 of the present invention thus provides a substantial number of rapidly interchangeable massage surface configurations in accordance with the desires and needs of the person receiving massage therapy. The vibratory device 10 is relatively simple in construction and lightweight for high portability.

A variety of further modifications and improvements to the invention described herein are believed to be apparent to those skilled in the art. For example, if desired, the non-rolling caps 48 and 50 depicted in FIG. 2 can be mounted within a cap case similar to the ball case 44 for mounting by threads or snap-fit or the like onto the base 38, wherein the cap case supports the non-rolling caps for rotation about a central longitudinal axis of the device. With this arrangement, limited freedom of motion of the caps 48 and 50 is thus permitted. Moreover, if desired, the cap 48 can be transparent to define a hollow internal chamber within which novelty items may be installed. Accordingly, no limitation is intended by way of the description and drawings, except as set forth in the appended claims.

What is claimed is:

1. A vibratory therapeutic device, comprising:
   a housing having air intake and discharge openings formed therein;
   a vibrator assembly mounted generally within said housing;
   a massage head disposed outside said housing and vibrated by said vibrator assembly; and
   means for supplying a flow of heated air into and around said massage head, said heated air flow supplying means including heating means within said housing and fan means for drawing air into said housing through said air intake opening for flow past heating relation with said heating means to elevate the temperature of the air, and for discharging the air from said housing through said air discharge opening;

said massage head including a mounting base secured to said housing and including means for removably supporting a massage member including a roller ball assembly having a ball case mounted upon said mounting base and a roller ball defining a massage surface carried by said ball case, said roller ball being for engagement with the body of a person receiving massage therapy, said mounting base and said ball case cooperatively defining a passage for flow of a portion of the air discharged from said housing through said discharge opening into said mounting base and further into contact with said roller ball while the remaining air is discharged adjacent to said massage head.

2. The device of claim 1 wherein said vibratory assembly and said air flow supply means collectively comprise a motor within said housing for rotationally driving an output shaft, said fan means including an unbalanced fan on said output shaft and rotatable therewith to vibrate the entire device and to create a flow of air between said housing intake opening and said housing discharge opening, and said heating means including heating elements within said housing for elevating the temperature of said air flow, said mounting base being secured to said housing generally at said housing discharge opening.

3. The device of claim 2 further including a rheostat for controlling operation of said motor and said heating elements.

4. The device of claim 1 further including a generally hemispherical cap for removable mounting onto said ball case over said roller ball, said cap defining a further massage surface.

5. The device of claim 4 further including a plurality of generally hemispherical caps each for removable mounting onto said ball case over said roller ball and respectively defining additional massage surfaces of different surface characteristics.

6. The device of claim 1 wherein said ball case is removably mounted on said mounting base and further including a plruality of massage members in addition to said roller ball for interchangeably mounting onto said mounting base.

7. The device of claim 6 wherein said plurality of massage members include a plurality of caps each of generally rounded shape and having massage surfaces of different surface characteristics.

8. The device of claim 1 further including a flexible bag including first means and second means for respectively closing opposite ends thereof, said bag being sized and shaped for receiving and carrying said housing with said first and second means in closed positions, said first means being adapted for removably mounting the associated end of said bag about a midportion of said housing with the opposite bag end draped about and extending beyond the massage head and with said second means in an open position whereby said bag forms a hood for concentrating the heated air flow in the region of the body portion receiving massage therapy.

* * * * *